US010022377B2

(12) United States Patent
Malhotra et al.

(10) Patent No.: US 10,022,377 B2
(45) Date of Patent: Jul. 17, 2018

(54) METHOD OF TREATING HYPERTENSION

(71) Applicant: Cipla Limited, Mumbai (IN)

(72) Inventors: Geena Malhotra, Mumbai (IN); Kalpana Joshi, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/361,020

(22) Filed: Nov. 24, 2016

(65) Prior Publication Data

US 2017/0157125 A1 Jun. 8, 2017

(30) Foreign Application Priority Data

Dec. 2, 2015 (IN) ........................ 4548/MUM/2015

(51) Int. Cl.
*A61K 31/519* (2006.01)
*A61K 9/20* (2006.01)

(52) U.S. Cl.
CPC .......... *A61K 31/519* (2013.01); *A61K 9/2018* (2013.01); *A61K 9/2027* (2013.01); *A61K 9/2054* (2013.01)

(58) Field of Classification Search
CPC ................................................... A61K 31/519
See application file for complete search history.

(56) References Cited

U.S. PATENT DOCUMENTS

2009/0324710 A1* 12/2009 Glidden ............... A61K 9/4808 424/451

OTHER PUBLICATIONS

Dingli et al. (CHEST 2001; 120; 801-808).*

* cited by examiner

*Primary Examiner* — Valerie Rodriguez-Garcia
(74) *Attorney, Agent, or Firm* — Meunier Carlin & Curfman LLC

(57) ABSTRACT

Disclosed herein are compositions and methods for the treatment of pulmonary hypertension, including pulmonary arterial hypertension. The methods include administering to a patient in need thereof an effective amount of anagrelide or derivative thereof. The compositions include an effective amount of anagrelide or derivative thereof, in some instances combined with one or more additional agents for the treatment of pulmonary hypertension.

10 Claims, No Drawings

METHOD OF TREATING HYPERTENSION

CROSS REFERENCE TO RELATED APPLICATION

This application claims the benefit of Indian Application 4548/MUM/2015, filed on Dec. 2, 2015, the content of which are incorporated herein in its entirety.

FIELD OF THE INVENTION

The present invention relates to a method of treatment of pulmonary hypertension, including pulmonary arterial hypertension, by administering a platelet-aggregation inhibitor agent either alone or optionally in combination with one or more other agents. In particular, the present invention pertains to methods for the treatment of pulmonary arterial hypertension in humans by administering anagrelide or derivative thereof, alone or in combination with one or more drugs.

BACKGROUND

Pulmonary arterial hypertension (PAH), one of the five types of pulmonary hypertension (PH), is a life-threatening disease characterized by pulmonary vascular remodeling that leads to increased pulmonary vascular resistance and pulmonary arterial pressure, most often resulting in right-side heart failure. It is a progressive condition characterized by elevated pulmonary arterial pressures leading to right ventricular (RV) failure. It is defined at cardiac catheterization as a mean pulmonary artery pressure of 25 mm Hg or more. The most common symptom associated is breathlessness, with impaired exercise capacity as a hallmark of the disease.

PAH is associated with significant morbidity and mortality. It is caused by complex pathways that culminate in structural and functional alterations of the pulmonary circulation and increases in pulmonary vascular resistance and pressure. Many mechanisms can lead to elevation of pulmonary pressures. In PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. Diverse genetic, pathological, or environmental triggers stimulate PAH pathogenesis culminating in vasoconstriction, cell proliferation, vascular remodeling, and thrombosis. Current concepts suggest that PAH pathogenesis involves three primary processes: vasoconstriction, cellular proliferation/vascular remodeling, and thrombosis.

The molecular mechanism underlying PAH pathophysiology is not known yet, but it is believed that the endothelial dysfunction results in a decrease in the synthesis of endothelium-derived vasodilators such as nitric oxide and prostacyclin. Moreover, stimulation of the synthesis of vasoconstrictors such as thromboxane and vascular endothelial growth factor (VEGF) results in a severe vasoconstriction and smooth muscle and adventitial hypertrophy characteristic of patients with PAH.

Better understanding of disease mechanisms led to subsequent classification of conditions with shared clinical and pathophysiological characteristics:

- Group 1: Pulmonary arterial hypertension (PAH), which can be idiopathic (IPAH) or associated with other conditions, notably systemic sclerosis and congenital heart disease
- Group 2: Pulmonary hypertension owing to left heart disease (PH-LHD)
- Group 3: Pulmonary hypertension owing to lung disease or hypoxia (PH-Lung), or both
- Group 4: Chronic thromboembolic pulmonary hypertension (CTEPH)
- Group 5: Unclear or multifactorial mechanisms.

Between 11% and 40% of patients with Idiopathic pulmonary arterial hypertension [IPAH] and 70% of patients with a family history of PAH carry a mutation in the gene encoding bone morphogenetic receptor-2 (BMPR2). However, penetrance is low, carriers have a 20% lifetime risk of developing pulmonary hypertension. Therefore, "multiple hits" are probably needed for the development of PAH. In pulmonary hypertension associated with left heart disease (PH-LHD), raised left atrial pressures result in secondary elevation of pulmonary pressure. In pulmonary hypertension owing to lung disease or hypoxia (PH-Lung), raised pulmonary arterial pressures result from mechanisms such as vascular destruction and hypoxic vasoconstriction. In chronic thromboembolic pulmonary hypertension [CTEPH], mechanical obstruction of the pulmonary vascular bed, is the primary process. Incidences are estimated to be 1-3.3 per million per year for IPAH and 1.75-3.7 per million per year for CTEPH; the prevalence of PAH is estimated at 15-52 per million. Pulmonary hypertension is more common in severe respiratory and cardiac disease, occurring in 18-50% of patients assessed for transplantation or lung volume reduction surgery, and in 7-83% of those with diastolic heart failure.

While there is currently no cure for PAH significant advances in the understanding of the pathophysiology of PAH have led to the development of several therapeutic targets. Besides conservative therapeutic strategies such as anticoagulation and diuretics, the current treatment paradigm for PAH targets the mediators of the three main biologic pathways that are critical for its pathogenesis and progression: (1) endothelin receptor antagonists inhibit the upregulated endothelin pathway by blocking the biologic activity of endothelin-1; (2) phosphodiesterase-5 inhibitors prevent breakdown and increase the endogenous availability of cyclic guanosine monophosphate, which signals the vasorelaxing effects of the down regulated mediator nitric oxide; and (3) prostacyclin derivatives provide an exogenous supply of the deficient mediator prostacyclin.

There are various drugs approved for the treatment of PAH: inotropic agents such as digoxin aids in the treatment by improving the heart's pumping ability. Nifedipine (Procardia) and Diltiazem (Cardizem) act as vasodilators and lowers pulmonary blood pressure and may improve the pumping ability of the right side of the heart.

Bosentan (Tracleer), ambrisentan (Letairis), macitentan (Opsumit), etc. are dual endothelin receptor antagonist that help to block the action of endothelin, a substance that causes narrowing of lung blood vessels. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relax pulmonary smooth muscle cells, which leads to dilation of the pulmonary arteries.

In addition to these established current therapeutic options, a large number of potential therapeutic targets are being investigated. These novel therapeutic targets include soluble guanylyl cyclase, phosphodiesterases, tetrahydrobiopterin, 5-hydroxytryptamine (serotonin) receptor 2B, vasoactive intestinal peptide, receptor tyrosine kinases, adrenomedullin, rho kinase, elastases, endogenous steroids, endothelial progenitor cells, immune cells, bone morphogenetic protein and its receptors, potassium channels, metabolic pathways, and nuclear factor of activated T cells.

Despite a certain success achieved in recent years, many patients with PAH are not adequately managed with existing therapies.

Anagrelide is commercialized under the brand name AGRYLIN® 0.5 mg Capsules. It is indicated for the treatment of patients with thrombocythemia, secondary to myeloproliferative neoplasms, to reduce the elevated platelet count and the risk of thrombosis and to ameliorate associated symptoms including thrombo-hemorrhagic events. The recommended starting dosage of AGRYLIN® is 0.5 mg four times daily or 1 mg twice daily in adults and 0.5 mg daily as starting dose in pediatric population. Clinically, AGRYLIN (anagrelide hydrochloride capsules) was found to be an effective, highly specific platelet-reducing agent. Anagrelide's effects on platelets are fully reversible. Moreover, it has no clinically significant effect on the other formed elements in the blood. These findings were demonstrated both preclinically and clinically.

Preclinical pharmacology data that are available demonstrate anagrelide's specificity toward platelets. While anagrelide was found to be a potent inhibitor of platelet aggregation, it had no significant effect on other cellular components of the blood. Additional significant pharmacologic effects attributed to anagrelide administration are hypotension and positive inotropic activity.

Two major metabolites, one active and one inactive, have been identified. The active metabolite, BCH24426 or 3-hydroxy anagrelide, shows similar potency and efficacy as anagrelide in the platelet lowering effect. Exposure as measured by plasma AUC is approximately 2-fold higher for 3-hydroxy anagrelide (BCH24426) compared to anagrelide. The inactive metabolite, RL603 or 5,6-dichloro-3,4-dihydroquinazolin-2-ylamine, does not participate in the overall effect of AGRYLIN.

It is an object of the invention to provide a novel therapeutic method for the treatment of pulmonary hypertension, including pulmonary arterial hypertension.

It is an object of the invention to provide novel compositions for the treatment of pulmonary hypertension, including pulmonary arterial hypertension.

It is an object of the invention to provide a novel therapeutic method for the treatment of pulmonary hypertension, including pulmonary arterial hypertension, using platelet reducing agents.

It is an object of the invention to provide novel compositions for the treatment of pulmonary hypertension, including pulmonary arterial hypertension, containing platelet reducing agents.

It is an object of the invention to provide a novel therapeutic method for the treatment of pulmonary hypertension, including pulmonary arterial hypertension, using anagrelide or derivative thereof.

It is an object of the invention to provide novel compositions for the treatment of hypertension, including pulmonary arterial hypertension, containing anagrelide or a derivative thereof.

SUMMARY

Disclosed herein are methods for treating pulmonary hypertension, for instance, pulmonary arterial hypertension, in patients in need thereof In some instances, the methods include at least partial reduction of the symptoms associated with pulmonary hypertension, and in some instances include completed elimination of the symptoms associated with pulmonary hypertension. The methods include the use of anagrelide or a derivative thereof for the treatment of pulmonary hypertension. Also disclosed herein are compositions for the treatment of hypertension, wherein the compositions include anagrelide or a derivative thereof.

The details of one or more embodiments are set forth in the descriptions below. Other features, objects, and advantages will be apparent from the description and from the claims.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Anagrelide is a selective inhibitor of phosphodiesterase 3A (PDE3A). Anagrelide works by inhibiting PDE3 found in platelets and as a result raises cAMP levels, which in turn may explain the inhibitory effect on platelet aggregation. Platelet aggregation is inhibited in humans at doses higher than those required to reduce platelet count. PDE3 is clinically significant because of its role in regulating heart muscle, vascular smooth muscle and platelet aggregation. PDE3A is mainly implicated in cardiovascular function and fertility. PDE3A is one of the therapeutic targets of PAH as well since it hydrolyzes cAMP and cGMP into AMP and GMP, respectively and thereby implicated in vasoconstriction of pulmonary artery smooth muscle cells.

The present inventors have found that the PDE3A antagonistic activity of anagrelide exhibits a significant role in the treatment of PAH.

As a result of its high expression in both the vasculature and the airways, PDE3 was identified as a potential therapeutic target in cardiovascular disease and asthma, and indeed, PDE3 inhibitors have subsequently been shown to relax vascular and airway smooth muscle, inhibit platelet aggregation and induce lipolysis.

The term "combination" as used herein, defines either a fixed combination in one dosage unit form, a non- fixed combination or a kit containing individual parts for combined administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of pulmonary arterial hypertension. Within the meaning of the present invention, the term "treat" also includes to arrest, delay the onset (i.e., the period prior to clinical manifestation of a disease) and/or reduce the risk of developing or worsening a disease.

The term "anagrelide" refers to a compound having the formula:

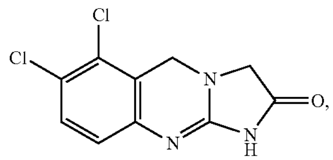 [SMILES: O=C1CN2Cc3c(ccc(Cl)c3Cl)N=C2N1]

or a pharmaceutically acceptable salt thereof. Unless specified to the contrary, the term "anagrelide" embraces both the free base and pharmaceutically acceptable salts thereof. An anagrelide derivative includes active metabolites of anagrelide, as well as compounds that convert in vivo either to anagrelide or an active metabolite thereof. In some instance, the anagrelide derivative can be a compound of Formula (1):

Formula (1)

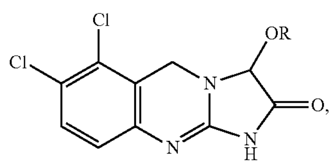

or a pharmaceutically acceptable salt thereof, wherein R is hydrogen, $(CO)R^1$, $(CO)OR^1$, or $PO_3X_2$;

$R^1$ is optionally substituted $C_{1-8}$alkyl, optionally substituted $C_{1-8}$alkaryl, optionally substituted $C_{3-8}$cycloalkyl, optionally substituted $C_{2-12}$heterocyclyl, optionally substituted $C_{2-12}$heteroaryl;

X is independently selected from hydrogen, pharmaceutically acceptable cation, or $R^1$ (as defined above). Unless specified to the contrary, the term "anagrelide derivative" embraces both the free base and pharmaceutically acceptable salts thereof.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. Pharmaceutically acceptable cations include the cationic component of the acids listed above. Pharmaceutically acceptable anions include the anionic component of the bases listed above. In some preferred embodiments, anagrelide (or a derivative thereof) is formulated as the hydrochloride salt.

Pulmonary hypertension can be classified as either primary or secondary. When the arterial hypertension is not accompanied or caused by another underlying heart or lung disease or condition, it is called primary pulmonary arterial hypertension. When the arterial hypertension is triggered by another disease state, it is designated secondary arterial pulmonary hypertension. Exemplary conditions which can cause secondary pulmonary hypertension include congenital heart defects, ventricular or atrial septal defects/holes, which are in some cases called Eisenmenger complex, as well as valve conditions such as stenosis.

Pulmonary hypertension can be associated with left heart disease, or right heart disease. In some embodiments, anagrelide (or a derivative thereof) can be used to treat pulmonary hypertension associated with left heart disease, whereas in other embodiments, anagrelide (or a derivative thereof) can be used to treat pulmonary hypertension associated with right heart disease. In further embodiments, anagrelide (or a derivative thereof) can be used to treat pulmonary hypertension associated with both right and left heart disease.

Pulmonary hypertension can be characterized by a pulmonary blood pressure greater than about 25 mm Hg at rest, and 30 mm Hg during exercise. Normal pulmonary arterial pressure is about 8-20 mm Hg at rest. In certain embodiments, anagrelide (or a derivative thereof) can be used to treat patients having a resting pulmonary arterial pressure of at least 25 mm Hg, at least 30 mm Hg, at least 35 mm Hg, at least 40 mm Hg, at least 45 mm Hg, at least 50 mm Hg, at least 55 mm Hg, or at least 60 mm Hg.

The dosage and dosage regimen may be calculated per kg body weight.

The dosage regimen may vary from a day to a month. Accordingly, the initial dosage and maintenance doses may be specified. For instance, an initial dosage may be administered over the course of 1, 3, 5, 7, 10, 14, 21 or 28 days, followed by a maintenance dosage which is administered for the duration of the treatment.

Preferably, the composition as contemplated by the invention may be administered at least once, twice or thrice a day in the dosing range from 0.05 to 20 mg or from 1 to 15 mg or as per the requirement of the patient to be treated.

Preferably, anagrelide (or a derivative thereof) may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

In some instances, anagrelide (or a derivative thereof) can be administered by inhalation, for instance as a powder or aerosolizable formulation.

The bioavailability of the drug in a composition, depends on various attributes of the drug as well as the other inactive ingredients in the formulation. The particle size of the drug is one of such attribute that may affect the bioavailability of the drug, when administered to a patient. The particle size may thus be adjusted as per the requirements of the invention.

The inventors of the present invention have also found that the solubility properties of anagrelide (or a derivative thereof) may be improved by nanosizing thus leading to better bioavailability and dose reduction of the drug.

In one embodiment, anagrelide (or a derivative thereof) may be present in the form of nanoparticles which have an average particle size of less than 2000 nm, less than 1500 nm, less than 1000 nm, less than 750 nm, or less than 500 nm.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof. Preferably, the composition as contemplated by the invention may be administered at least once, twice or thrice a day, in a dosing range of 0.05 to 20 mg or from 1 to 15 mg or as per the requirement of the patient to be treated. On administration, anagrelide prodrugs (i.e., compounds of Formula (1) in which R is not hydrogen) hydrolyzes to the active moiety, 3-hydroxyanagrelide. The dose calculation is done taking the above into consideration, and the anagrelide prodrug is administered as a weight equivalent to the parent 3-hydroxyanagrelide.

Disclosed herein are methods for treating patients with pulmonary arterial hypertension. The hypertension may be mild (resting arterial pressure between 20 -25 mm Hg) or complete (resting arterial pressure greater than 25 mm Hg). The patient to be treated may have a pulmonary arterial pressure greater than 25 mm Hg, greater than 28 mm Hg, greater than 30 mm Hg, greater than 32 mm Hg, greater than 34 mm Hg, greater than 36 mm Hg, greater than 38 mm Hg, or greater than 40 mm Hg.

Anagrelide (or a derivative thereof) can be used to treat patients with sporadic idiopathic PAH, heritable PAH, as well as PAH due to disease of small pulmonary muscular arterioles. In some embodiments, anagrelide (or a derivative thereof) is administered to a patient (which may be a human or other mammal) in an amount sufficient to cause at least a 5%, 10%, 15%, 20%, 25%, 30%, 35%, or 40% reduction in resting arterial pressure relative to the pulmonary arterial pressure prior to commencing treatment. In some instances, anagrelide (or a derivative thereof) is administered at a dose effective such that the patient's final resting arterial pressure is about 25 mm Hg, about 24 mm Hg, about 23 mm Hg, about 22 mm Hg, about 21 mm Hg, about 20 mm Hg, about 19 mm Hg, about 18 mm Hg, about 17 mm Hg, about 16 mm Hg, about 15 mm Hg, or about 14 mm Hg. In certain embodiments, anagrelide (or a derivative thereof) is administered in combination with other agents, as described below, to achieve these therapeutic outcomes.

In some instances, the anagrelide (or a derivative thereof) may be administered to a patient a single time, while in other cases anagrelide (or a derivative thereof) can be administered using an intervallic dosing regimen. For instance, anagrelide (or a derivative thereof) may be administered once, twice, or three times a day for a period at least 1 week, for example 2 weeks, 4 weeks, 6 weeks, 8 weeks, 10 weeks, 20 weeks, 40 weeks, or 52 weeks. In some instances, anagrelide (or a derivative thereof) administration can be suspended for some period of time (e.g., 1, 2, 3, 4, 6, 8, 10, 20, 40 or 52 weeks) followed by another period of administration.

In some instances, the anagrelide (or a derivative thereof) can be administered to the patient using an interval greater than a day. For instance, the anagrelide (or a derivative thereof) can be administered once every other day, once every third day, once a week, once every two weeks, once every four weeks, once a month, once every other month, once every third month, once every six months, or once a year. In some instance injectable formulations, such as depot formulations, are suitable for dosing regimens with extended periods in between administration, however, oral formulations can also be used in such systems.

In some embodiments, pulmonary arterial hypertension can be alleviated or treated by administration of anagrelide (or a derivative thereof) in combination with one or more other drugs either simultaneously, sequentially, or separately.

Preferably, one or more standard of care drugs that may be envisaged under the scope of the present invention may comprise from categories of for the treatment of pulmonary hypertension such as, but not limited to phosphodiesterase inhibitors, endothelin receptor antagonist, Inotropic agents, and stimulators of soluble guanylate cyclase, such as riociguat.

Specifically, one or more standard of care drugs include but not limited to sildenafil, tadalafil, bosentan, ambrisentan, macitentan, nifedipine, diltiazem, digoxin. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relaxes pulmonary smooth muscle cells, which leads to dilation of the pulmonary arteries.

The use of anagrelide may preferably be associated with one or more of the above referenced drugs as a combination therapy (either of the same functional class or other) depending on various factors like drug-drug compatibility, patient compliance and other such factors wherein the said combination therapy may be administered either simultaneously, sequentially, or separately for the treatment of PAH.

Anagrelide (or a derivative thereof) may be provided with one or more drugs in the form of a kit, wherein the kit includes anagrelide and at least one other drug, and instructions for their administration to a PAH patient.

In certain embodiments, the administration of anagrelide (or a derivative thereof), either alone or in combination with one or more drugs selected from but not limited to phosphodiesterase inhibitors such as sildenafil, tadalafil etc., endothelin receptor antagonist such as bosentan, macitentan etc. and stimulators of soluble guanylate cyclase such as riociguat. In certain embodiments, anagrelide (or a derivative thereof) can be co-administered with one or more additional agents effective to lower pulmonary hypertension. In some embodiments the co-administration includes a unitary dosage form containing anagrelide (or a derivative thereof) and at least one more agent. In other embodiments, anagrelide (or a derivative thereof) is administered separately from the other agent(s). The additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, and sitaxsentan; guanylate cyclase stimulators such as riociguat; diuretics; toprimate; fusadil; or anti-coagulants like warfarin.

It may be well appreciated by a person skilled in the art that the pharmaceutical composition comprising anagrelide in combination with one or more drugs may require specific dosage amounts and specific frequency of administrations specifically considering their individual established doses, the dosing frequency, patient adherence and the regimen adopted. As described herein, considering that there are various parameters to govern the dosage and administration of the combination composition as per the present invention, it would be well acknowledged by a person skilled in the art to exercise caution with respect to the dosage, specifically, for special populations associated with other disorders.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Pulmonary Arterial Hypertension Efficacy Model: Monocrotaline Rat

Method:

Adult male Sprague-Dawley rats (287±4 g) were obtained from Charles River Laboratories (Raleigh, N.C.). Animals housed individually in a temperature/humidity controlled room with 12-hour light/dark cycles, had free access to water and food and were acclimated for one week prior to the study. Rats were randomly assigned to one of the experimental groups (n=10 per group). Rats in groups 1 and 2 served as healthy controls; the remaining rats were injected subcutaneously on Day 0 with 60 mg/kg body weight monocrotaline, the toxic alkaloid of *Crotalaria spectabilis*, (dissolved in DMSO at a concentration of 60 mg/ml, Sigma Aldrich, St. Louis, Mo.). On days 1-21, the rats were dosed via oral gavage (2 ml/kg) with vehicle (PBS), or the test compound—Anagrelide. Rats were weighed daily, and the dosages of test compound adjusted appropriately.

Monocrotaline (MCT) is an 11-membered macrocyclic pyrrolizidine plant alkaloid. A single SQ injection into rats results in hepatic generation of toxic metabolite—MCT pyrrole. Phase II metabolism of MCT is through glutathione conjugation. Reactive metabolite is transported to lungs, injuring pulmonary vasculature.

Results:

Anagrelide was shown to prevent the development of PAH in the rat monocrotaline (MCT) model. Thus, Anagrelide, a phosphodiesterase 3A inhibitor, when administered to rats for three weeks in daily oral doses, prevents not only monocrotaline (MCT)-induced elevations in pressure in the pulmonary arterial circuit but also hypertrophy of the right ventricle.

Example 2

Hemodynamic Evaluation of Anagrelide in Anesthetized Sprague Dawley Rats Treated with Monocrotaline to Induce Pulmonary Arterial Hypertension Method:

The effects of sildenafil and anagrelide were evaluated in rats with monocrotaline induced pulmonary arterial hypertension. Male Sprague-Dawley rats were orally administered vehicle (variable, see below), anagrelide (1 mg/kg given once daily for 28 days or 2 mg/kg total daily dose, divided into a BID regimen given every day for 28 days starting on Day 1), or sildenafil (30 mg/kg, administered twice daily) (n=10 in each group). Rats received a single injection of monocrotaline (60 mg/kg, s.c.) on Study Day 1. On the twenty-eighth day following monocrotaline dosing, the rats were anesthetized with ketamine/xylazine for terminal monitoring of pulmonary and systemic arterial pressures along with heart rate. The study design for the test article and vehicle administrations are detailed below:

| Group | Test Compound | Test Compound Dose Level (mg/kg) | Dose Conc. (mg/mL) | Dose Volume (mL/kg) | Dose Period | Dose Route | Dose Days | No. of Male Rats |
|---|---|---|---|---|---|---|---|---|
| 2-5 | Monocrotaline[1] | 80 | 80 | 1 | AM | SC | 1 | 100 |
| 1 | DMSO[2] | NA | NA | 1 | AM | SC | 1 | 5 |
| 2 | Vehicle | NA | NA | 5 | AM | Oral | 1-28 | 10 |
| 3 | Anagrelide | 1 | 0.2 | 5 | AM | Oral | 1-28 | 10 |
| | | | | 5 | PM | | | |
| 4 | Anagrelide | 1 | 0.2 | 5 | AM | Oral | 1-28 | 10 |
| | | 1 | 0.2 | 5 | PM | | | |
| 5 | Sildenafil | 30 | 6 | 5 | AM | Oral | 1-28 | 10 |
| | | 30 | 6 | 5 | PM | | | |

[1]Single dose in DMSO administered 28 days prior to terminal procedure.

[2]Single dose administered 28 days prior to terminal procedure.

Results:

There were differences in systolic and mean pulmonary arterial pressures after 28 days in rats treated with anagrelide at 2 mg/kg/day given BID compared to the vehicle group. Rats treated with anagrelide showed a reduction at this dose with systolic pulmonary arterial pressure—the variable used as an arbiter of protection. There was paradoxically no effect with respect to right ventricular hypertrophy (as measured by RV/LV+S—Fulton's Index) in the anagrelide group (no change) compared to vehicle. When correcting RV (wt) by body weight, anagrelide showed a decrease in hypertrophy at either dose. Mean arterial pressure was lower in rats treated with anagrelide compared to vehicle.

| Parameter Mean ± SEM | Treatment Cohort - Vehicle (mg/kg) DMSO |
|---|---|
| Systolic PAP (mm Hg) | 16 ± 2 |
| Mean PAP (mm Hg) | 14 ± 2 |
| MAP (mm Hg) | 84 ± 9 |
| HR (bpm) | 313 ± 13 |
| Heart Wt (g) | 1.17 ± 0.03 |
| HW/BW | 2.75 ± 0.07 |
| LV Wt (g) | 0.82 ± 0.01 |
| RV Wt (g) | 0.22 ± 0.02 |
| Lung Wt (g) | 1.65 ± 0.08 |
| RV/LV + S | 0.26 ± 0.02 |
| RV/BW | 0.50 ± 0.03 |
| Body Weight (kg) | 0.43 ± 0.01 |

| Parameter Mean ±SEM | Treatment Cohort (mg/kg) Vehicle | Anagrelide 1[#] | Anagrelide 2/day bid | Sildenafil 60/day bid |
|---|---|---|---|---|
| Systolic PAP (mm Hg) | 60 ± 2 | 44 ± 2 | 43 ± 4 | 46 ± 7 |
| Mean PAP (mm Hg) | 46 ± 1 | 36 ± 2 | 36 ± 2 | 38± 6 |
| MAP (mm Hg) | 70 ± 6 | 59 ± 5 | 52 ± 6 | 69 ± 5 |
| HR (bpm) | 274 ± 10 | 325 ± 28 | 258 ± 10 | 278 ± 21 |
| Heart Wt (g) | 1.36 ± 0.05 | 1.37 ± 0.03 | 1.21 ± 0.04* | 1.24 ± 0.02 |
| HW/BW | 4.43 ± 0.15 | 4.34 ± 0.45 | 3.98 ± 0.24 | 3.89 ± 0.17 |
| LV Wt(g) | 0.78 ± 0.01 | 0.76 ± 0.01 | 0.69 ± 0.02* | 0.74 ± 0.02 |
| RV Wt (g) | 0.46 ± 0.02 | 0.47 ± 0.01 | 0.41 ± 0.02 | 0.38 ± 0.02* |
| Lung Wt (g) | 2.90 ± 0.53 | 2.10 ± 0.19 | 2.21 ± 0.07 | 2.36 ± 0.13 |
| RV/LV + S | 0.59 ± 0.03 | 0.62 ± 0.01 | 0.59 ± 0.04 | 0.51 ± 0.03 |
| RV/BW | 1.50 ± 0.06 | 1.49 ± 0.16 | 1.35 ± 0.12 | 1.19 ± 0.09 |
| Body Weight (kg) | 0.31 ± 0.02 | 0.32 ± 0.02 | 0.31 ± 0.01 | 0.32 ± 0.01 |

Example 3

Formulations

Compositions useful for treating pulmonary arterial hypertension can include the following ingredients:

| Ingredients | Qty/Tab (mg) |
|---|---|
| Anagrelide hydrochloride | 0.5-10 |
| Microcrystalline cellulose | 10-25 |
| Lactose Monohydrate | 20-80 |
| Lactose Anhydrous | 10-30 |
| Sodium lauryl sulfate (SLS) | 0.2-1.5 |
| Croscarmellose Sodium | 5-10 |
| Povidone | 3-10 |
| Aerosil 200 | 1-5 |
| Magnesium Stearate | 1-5 |

| Ingredients | Quantity Mg/tablet |
|---|---|
| Anagrelide hydrochloride | 0.5-10 |
| Lactose monohydrate | 10-50 |
| Microcrystalline cellulose (Avicel PH 102) | 20-60 |
| Croscarmellose sodium (Ac-Di-sol) | 5-20 |
| Polysorbate 80 | 0.5-2.0 |
| Povidone | 10-25 |
| Lactose anhydrous | 5-20 |
| Colloidal silicon dioxide (Aerosil 200) | 1-5 |
| Magnesium stearate | 2-8 |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating pulmonary arterial hypertension (PAH) characterized by a narrowing of the pulmonary arteries, in a patient in need thereof, comprising administering to the patient in need of such treatment a composition comprising an effective amount of anagrelide or a pharmaceutically acceptable salt thereof, wherein the patient has a resting pulmonary arterial pressure greater than 25 mm Hg, wherein the anagrelide or pharmaceutically acceptable salt thereof is administered in an amount effective to lower resting pulmonary arterial blood pressure at least 5% relative to the resting pulmonary arterial blood pressure prior to commencing treatment, and wherein the anagrelide or pharmaceutically acceptable salt thereof is administered in a dose from 0.05 to 20 mg.

2. The method of claim 1, wherein the patient has a resting pulmonary arterial pressure greater than 40 mm Hg.

3. The method of claim 1, comprising administering a composition comprising an effective amount of anagrelide to the patient in need thereof.

4. A method of treating pulmonary arterial hypertension (PAH) characterized by a narrowing of the pulmonary arteries, in a patient in need thereof, comprising administering to the patient in need of such treatment a composition comprising an effective amount of a compound of Formula (1):

Formula (1)

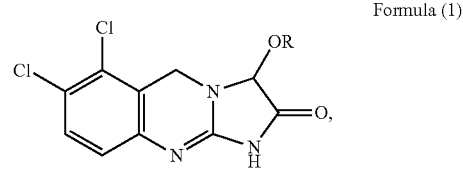

or a pharmaceutically acceptable salt thereof, wherein R is hydrogen, $C(O)R^1$, $C(O)OR^1$, or $PO_3X_2$;

$R^1$ is optionally substituted $C_{1-8}$alkyl, optionally substituted $C_{1-8}$alkaryl, optionally substituted $C_{3-8}$cycloalkyl, optionally substituted $C_{2-12}$heterocyclyl, optionally substituted $C_{2-12}$uheteroaryl;

X is independently selected from hydrogen, pharmaceutically acceptable cation, or $R^1$, where the patient has a resting pulmonary arterial pressure greater than 25 mm Hg, wherein the composition is administered in an amount effective to lower resting pulmonary arterial blood pressure at least 5% relative to the resting pulmonary arterial blood pressure prior to commencing treatment, and wherein the compound of Formula (1) is administered in a dose from 0.05 to 20 mg.

5. The method of claim 4, wherein R is hydrogen.

6. The method of claim 1, wherein the composition is administered orally.

7. The method of claim 1, wherein the composition is administered parenterally.

8. The method of claim 4, wherein the patient has a resting pulmonary arterial pressure greater than 40 mm Hg.

9. The method of claim 4, wherein the composition is administered orally.

10. The method of claim 4, wherein the composition is administered parenterally.

* * * * *